(12) United States Patent
Meswania

(10) Patent No.: US 7,662,189 B2
(45) Date of Patent: *Feb. 16, 2010

(54) MASSIVE MODULAR SYSTEM

(75) Inventor: Jay Meswania, St. Albans (GB)

(73) Assignee: Stanmore Implants Worldwide Ltd. (GB)

( * ) Notice: Subject to any disclaimer, the term of this patent is extended or adjusted under 35 U.S.C. 154(b) by 71 days.

This patent is subject to a terminal disclaimer.

(21) Appl. No.: 11/433,953

(22) Filed: May 15, 2006

(65) Prior Publication Data

US 2006/0235540 A1 Oct. 19, 2006

Related U.S. Application Data

(63) Continuation of application No. 10/450,559, filed on Jun. 12, 2003, now Pat. No. 7,044,976.

(51) Int. Cl.
*A61F 2/32* (2006.01)
(52) U.S. Cl. .............. 623/22.45; 623/22.42; 623/22.43
(58) Field of Classification Search .............. 623/22.45, 623/22.41, 22.42, 22.44, 22.46, 20.15, 20.25, 623/20.34, 20.36, 23.18, 23.22, 23.23, 23.25, 623/23.35, 23.34, 23.44, 23.45, 22.43
See application file for complete search history.

(56) References Cited

U.S. PATENT DOCUMENTS

| | | | | | |
|---|---|---|---|---|---|
| 4,878,917 | A | * | 11/1989 | Kranz et al. | 623/23.45 |
| 4,963,155 | A | * | 10/1990 | Lazzeri et al. | 623/22.42 |
| 5,201,767 | A | * | 4/1993 | Caldarise et al. | 623/23.35 |
| 6,071,311 | A | * | 6/2000 | O'Neil et al. | 623/20.15 |
| 6,613,092 | B1 | * | 9/2003 | Kana et al. | 623/20.15 |
| 6,682,568 | B2 | * | 1/2004 | Despres et al. | 623/22.42 |
| 7,044,976 | B2 | * | 5/2006 | Meswania | 623/22.45 |

* cited by examiner

*Primary Examiner*—Pedro Philogene
(74) *Attorney, Agent, or Firm*—Galgano & Associates, PLLC

(57) ABSTRACT

The specification discloses a modular system for the formation of a prosthesis for the replacement of a long bone in a human or animal body. The system provides a prosthesis comprising a proximal or distal end component such as a trochanter or condylar head, forming one component of a prosthetic joint, a shaft for assembly with the distal or proximal end component and a stem for engagement in a resected bone. The system allows the assembly of a custom fitted prosthesis from a limited range of components.

9 Claims, 8 Drawing Sheets

MASSIVE MODULAR SYSTEM

CROSS-REFERENCE TO RELATED APPLICATION

This application is a continuation application of application Ser. No. 10/450,559 filed Jun. 12, 2003, now issued U.S. Pat. No. 7,044,976.

BACKGROUND OF THE INVENTION

This invention relates to prostheses for partial or total replacement of a long bone in human or animal bodies.

In the case where limbs are badly damaged or large amounts of bone must be surgically removed, e.g., in the case of treatment of bone cancer, there is a need for prostheses which replace a large part of the natural bone and which can be assembled by the surgeon to meet a wide range of conditions. The present invention provides a modular system for constructing effectively customised prostheses to meet a range of such surgical requirements. Typical requirements may be, for example, to replace the proximal or distal femur or perhaps the total replacement of the femur.

BRIEF SUMMARY OF THE INVENTION

According to one aspect of the present invention there is provided a prosthesis for partial or total replacement of a long bone in humans or animals, said prosthesis comprising a proximal or distal end component forming one component of a prosthetic joint, a shaft assembled with the distal or proximal end and a stem for engagement in a resected bone, the shaft, stem and the distal or proximal end components being connected by male and female tapers, each male taper including a projection which extends longitudinally of the prosthesis but is offset from its axis and engages in a corresponding recess in the female taper, a cross-hole being provided for access transversely to the region of the end of the male taper by a disassembly tool, and wherein said projection maintains adjacent components in the desired angular relationship.

The invention also includes other features including a collar which may be assembled to the shaft or extension thereof, the collar being dimensioned to abut the resected face of bone into which the prosthesis is to be fitted, the collar having a portion adapted to taper towards the resected face and having a surface treatment designed to encourage bone growth over the tapered surface of the collar.

In the case of proximal femoral replacement prostheses, the prosthesis preferably includes a trochanter replacement component assembled with a shaft and stem, the trochanter replacement component being shaped to correspond approximately with an anatomical trochanter and including a femoral neck for receiving a femoral ball and a generally flat face opposite the femoral neck for connection to residual bone or soft tissue.

BRIEF DESCRIPTION OF THE DRAWINGS

Detailed features of prostheses in accordance with the invention will become apparent from the accompanying drawings, in which.

DETAILED DESCRIPTION OF THE INVENTION

Figure 1:
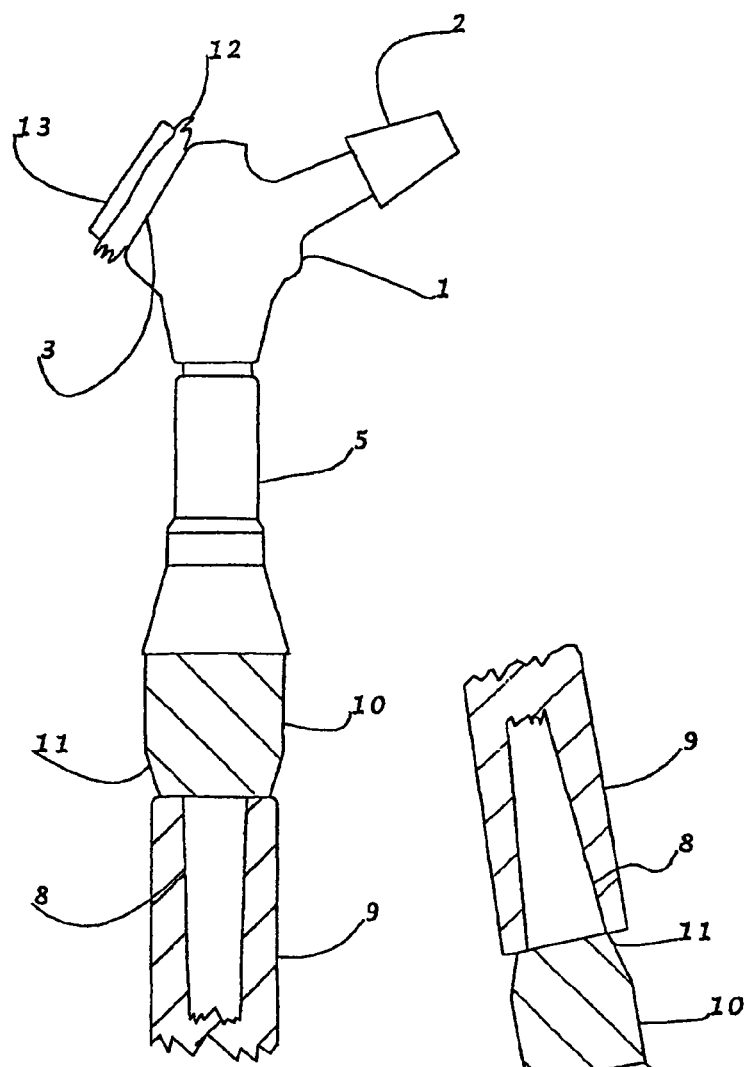
FIG. 1 is a side elevation of assembled components of a proximal femoral prosthesis.

Referring first to FIG. 1, this drawing shows diagrammatically an assembled, proximal femoral prosthesis comprising a trochanter component 1 having a femoral neck 2, which is tapered to receive a femoral ball in a conventional fashion. The trochanter component is shown in more detail in the views shown in FIGS. 3A and 3B and it may be seen that it corresponds roughly to the anatomical shape and has a generally flat face 3 for attachment to any residual bone or to soft tissues. The trochanter component 1 has an internal female taper, best seen in FIGS. 3A and 3B, and is assembled onto a male taper carried by a shaft 5. The detailed construction of shaft 5 are apparent from the views in FIGS. 4A and 4B and it will be seen that shaft 5 has a male taper 33 at one end for engagement into the female taper of the trochanter component 1 and at its other end has a female taper 7 for engagement with one end of a stem 8 (shown in more detail in FIG. 5).

Figure 6:
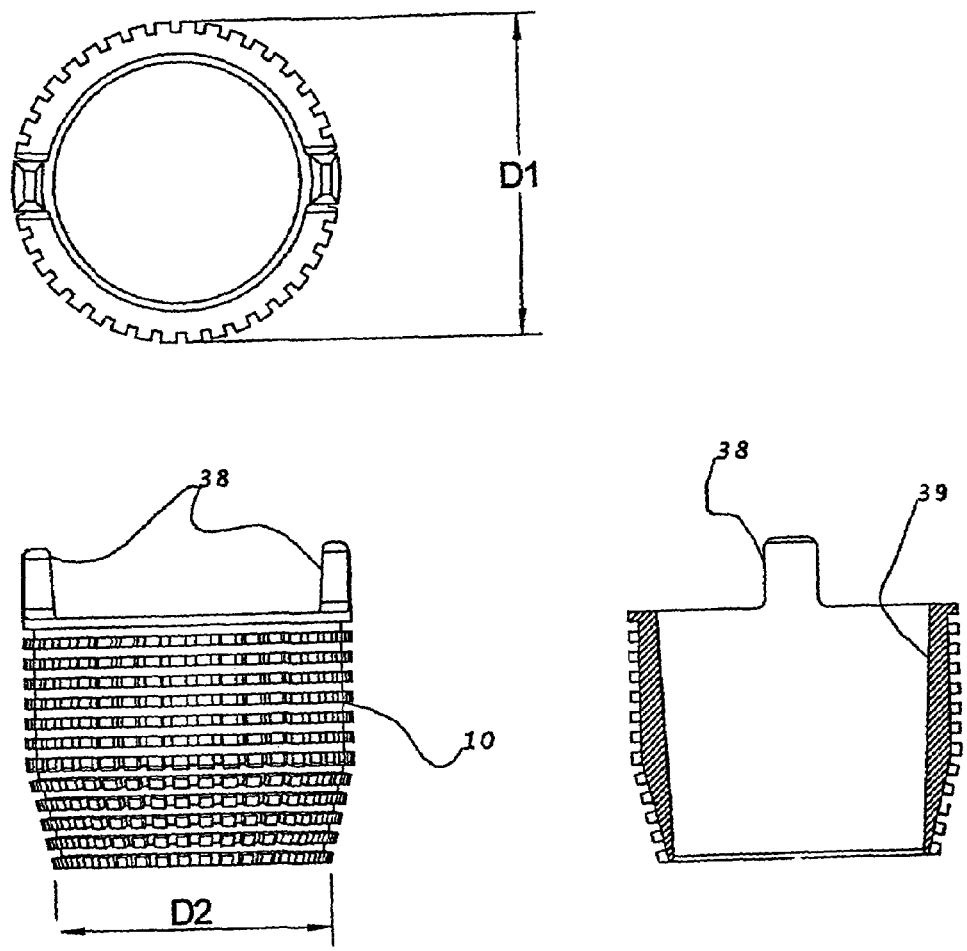
FIG. 6 shows various views of a collar for use in the prosthesis in accordance with the invention and FIG. 7 shows several views of a modular extension shaft for use in the present invention.

Stem 8 is fitted into a resected femur 9 either by press-fit or by using bone cement. Surrounding the distal end of the shaft 5, is a collar 10 which is shown in more detail in FIG. 6. Collar 10 has a distal lower end 11 which abuts cancellous bone forming the face of resected bone 9. The dimensions of collar 10 are selected so that the end face of collar 10 terminates in board of the external dimension of the bone 9. Collar 10 is formed on its external surface with stipples or a bone growth stimulating material such as hydroxyapatite. These measures encourage cancellous bone to grow over the surface of collar 10 and help to more firmly lock the prosthesis into the residual resected bone 9.

It is often possible when removing damaged bone or tumour to retain the residual portion 12 of the trochanter. This residual piece of bone may have ligaments or other soft tissue attached to it and it is useful to use this to assist in stabilising the trochanter replacement component. The residual bone 12 can be attached to the trochanter component by clamping a plate 13 to the face 3 of the trochanter component.

Figure 2:
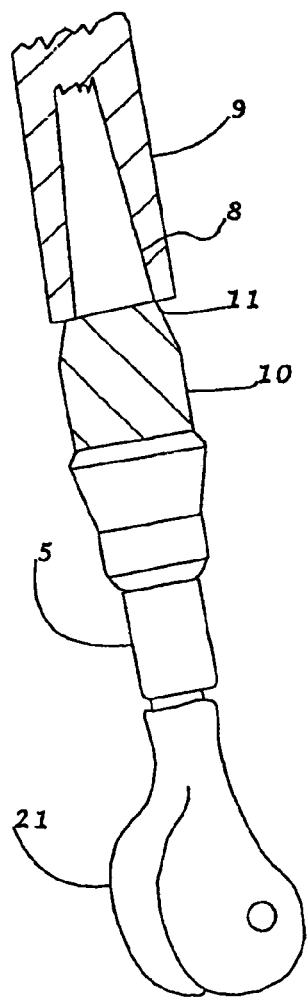
FIG. 2 is a side elevation of a distal femoral prosthesis in accordance with the invention.

FIG. 2 shows a view of an assembled distal prosthesis comprising a condylar head component 21 forming one part of the knee joint which is connected to a shaft 5 in an analogous way to the way in which the trochanter component 1 is connected to the shaft 5 in FIG. 1. Similarly, shaft 5 is connected to stem 8 in a similar way to that previously described in connection with FIG. 1 and collar 10 is slid over the tapered lower portion of shaft member 5 just as described above in connection with FIG. 1 and has a distal tapered portion 11 which abuts the resected face of the femur 9. In a similar way, this encourages bone growth over the surface of the collar 10.

Figure 3A:
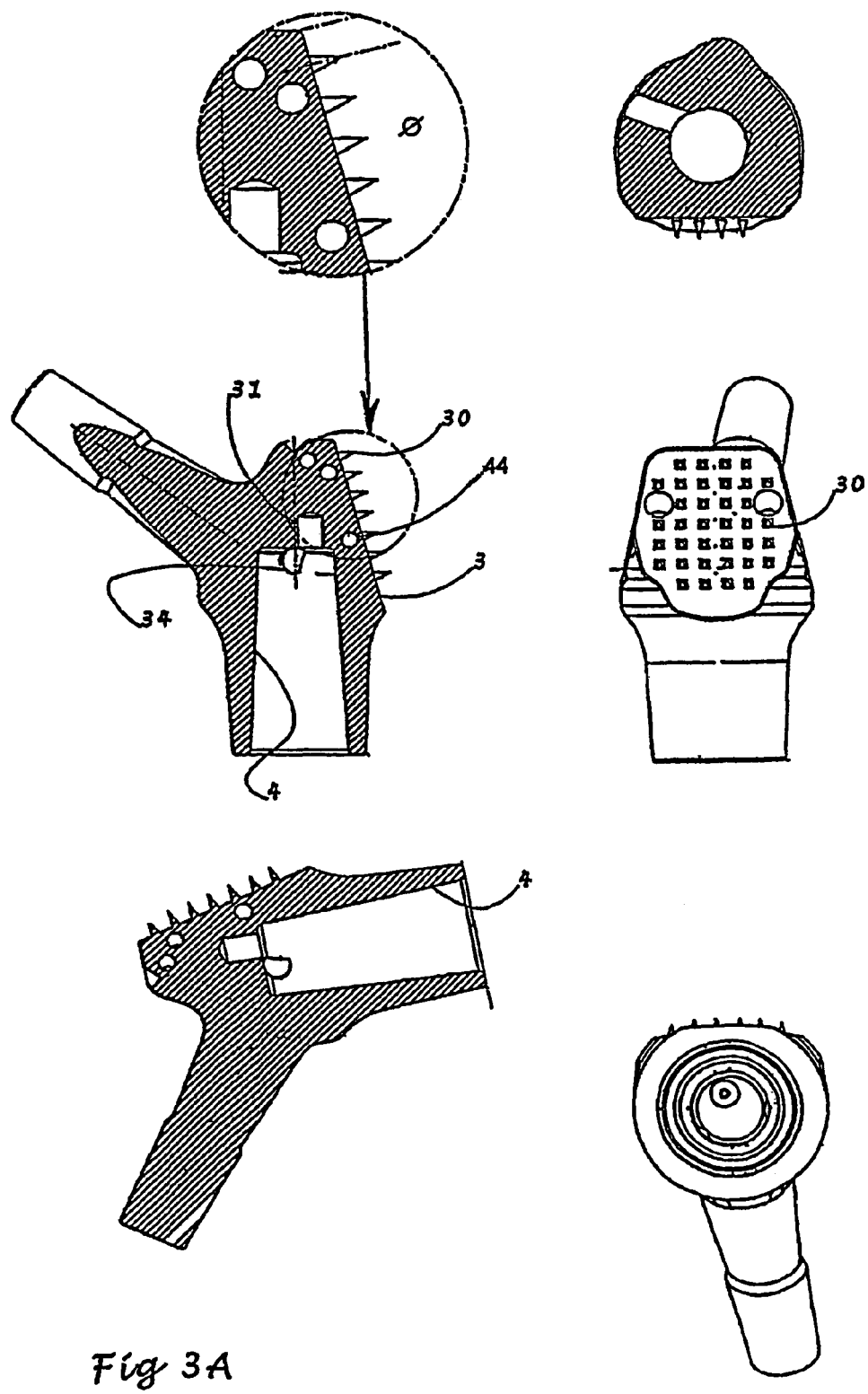
FIGS. 3A and 3B show various views of a trochanter replacement component in accordance with the invention.
Figure 3B:
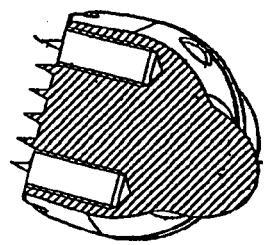
Figure 3B:
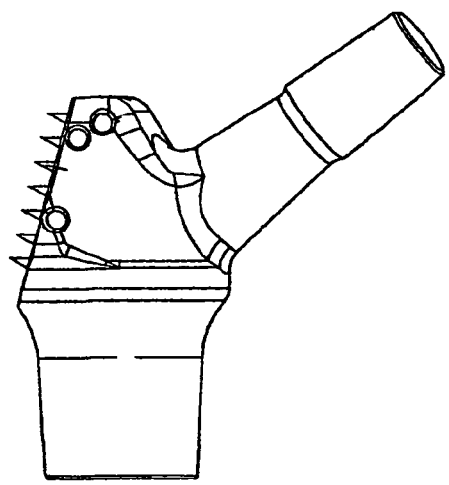
Figure 3B:
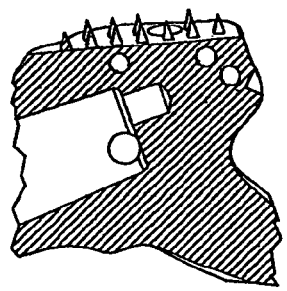
Figure 3B:
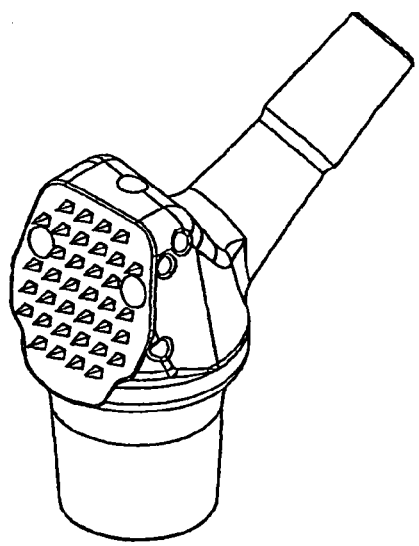
Figure 4A:
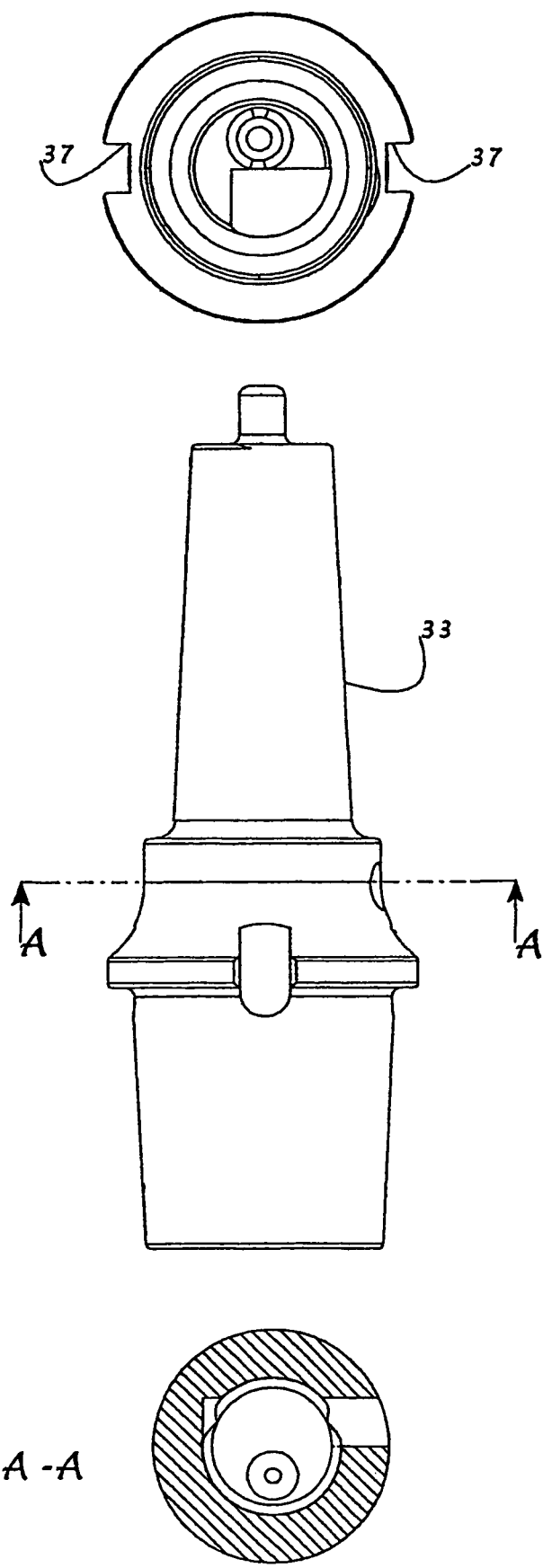
FIGS. 4A and 4B show various views of a modular shaft for use in the present invention.
Figure 4B:
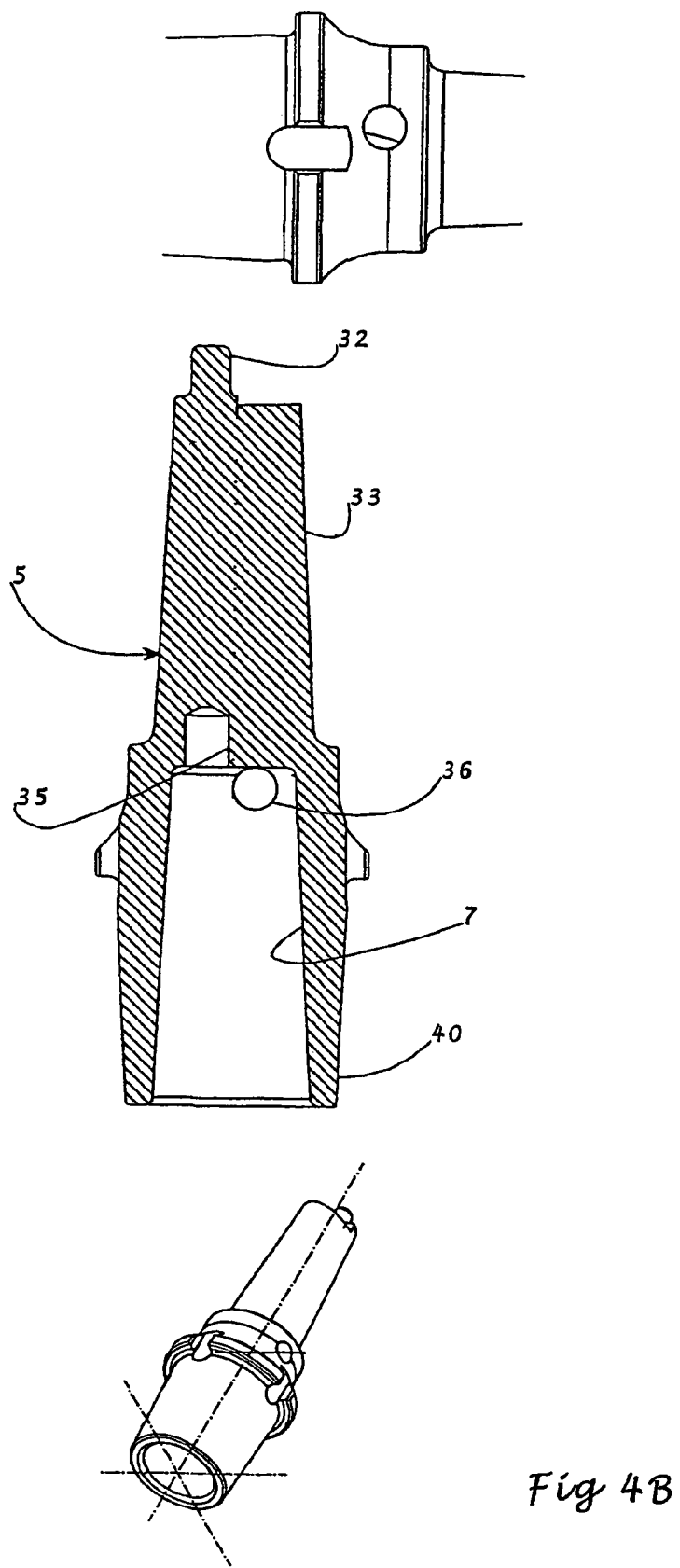

Details of the trochanter component 1 are shown in the views of FIGS. 3A and 3B. It would be seen that the flat face 3 of the trochanter component 1 are formed in a pattern of spikes 30. This pattern of spikes is provided to ensure a firm connection with any residual bone 12 (see FIG. 1) and serves to further stabilize the prosthesis. It would be seen that the trochanter component has a female taper terminating internally with an offset recess 31. Recess 31 is shaped to be engaged with a projection 32 formed on the male taper 33 of the shaft 5. (See FIGS. 4A and 4B). The trochanter component is provided with a transverse hole 34 into which a disassembly tool can be inserted to force the trochanter component and the shaft apart where disassembly is required. As can be seen in FIGS. 4A and 4B, the shaft 5 also has a female taper 7 and is formed with a similar recess 35 to the recess 31 in the trochanter component. Shaft 5 also includes a transverse hole 36 into which a disassembly tool can be inserted to force apart the shaft and the stem component which is designed to fit into the taper 7.

Referring further to FIGS. 3A and 3B, it would be seen that the trochanter component also incorporates holes 36. These are intended for suturing the trochanter component to soft tissue such as tendons in the event that there is no residual bone, to which tendons are attached, which could be clamped to the stippled face 3.

The trochanter component is intended to be provided as a standard component of a modular system although there would be right and left handed versions. There may also be alternative trochanter components in which the degree of offset of the femoral neck differs to suit a particular patent.

As can be seen from FIGS. 4A and 4B, the femoral shaft, although standardized so far as the tapers are concerned, is supplied in lengths of 15 mm intervals. The femoral shaft is also provided with notches 37 designed to engage with corresponding ears 38 which are integral with the collar 10. As can be seen from FIG. 6, collar 10 has an internal taper 39 adapted to fit on a corresponding taper 40 at one end of the shaft 5. The engagement of the collar on the shaft 5 and also the ears 38 in the notches 37 enables the collar to be fitted securely on the shaft. As can be seen from FIG. 6, the collar is supplied in a number of diameters, D1 and D2.

Figure 5:
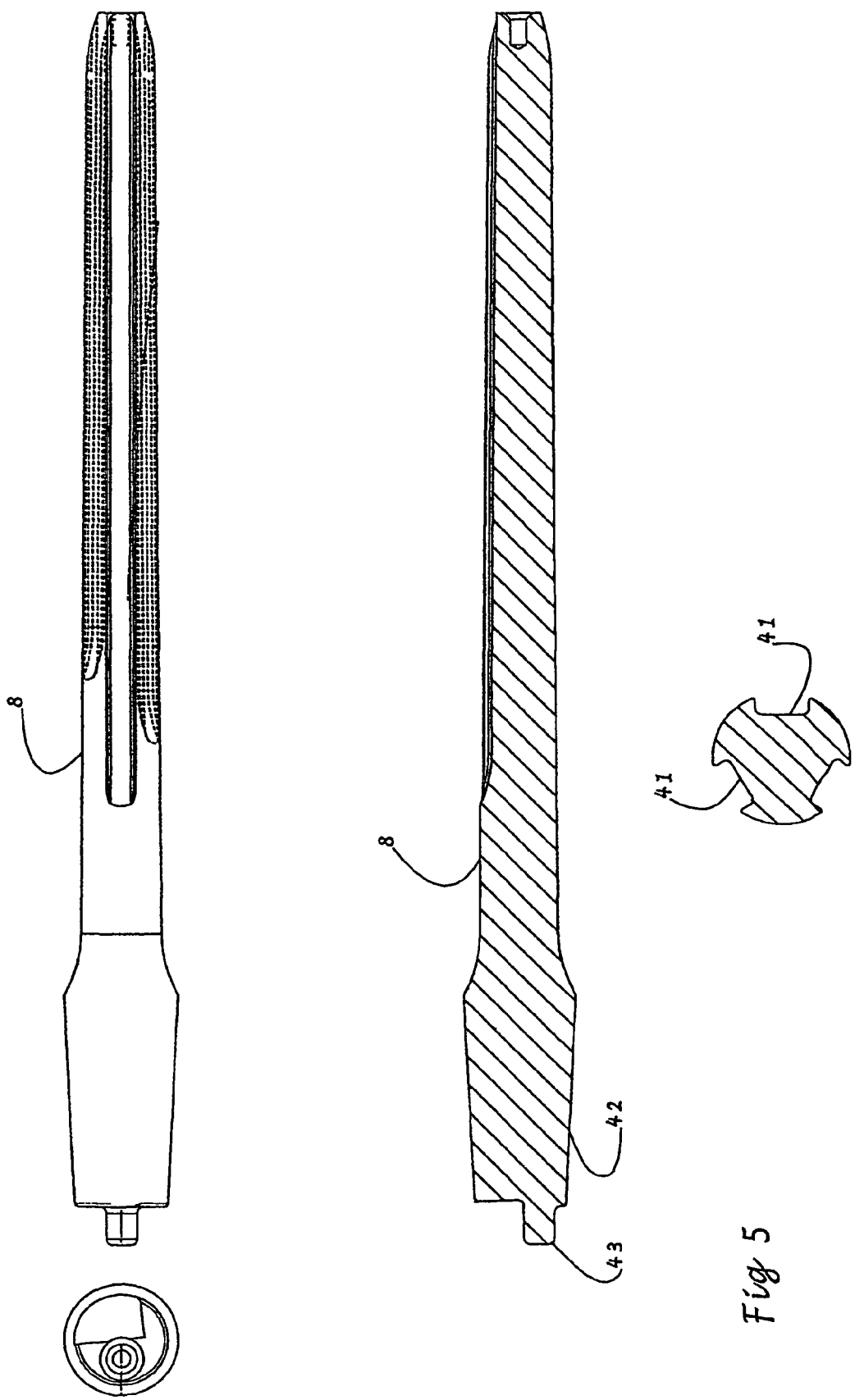
FIG. 5 shows various views of a femoral stem for use in the present invention.

FIG. 5 shows various views of the stem component 8. As can be seen from the cross-sectional view, the stem is formed with flutes for engaging in cortical bone and may be straight or curved to accommodate any curvature in the bone canal. The proximal end of the stem has a taper 42 which corresponds with the internal taper 7 of the shaft component. The stem also includes a projection 43 which corresponds with the recess 35 in the shaft component. The shaft component 5 includes a transverse hole 36 for disassembly purposes whereby a tool inserted through the hole will press apart the stem and the shaft by bearing on the corresponding end faces of the stem and shaft. As can be seen from FIG. 5, the stem is available in a number of diameters and lengths and may be curved or straight to accommodate the various surgical problems which might be encountered in fitting such a prosthesis.

Figure 7:
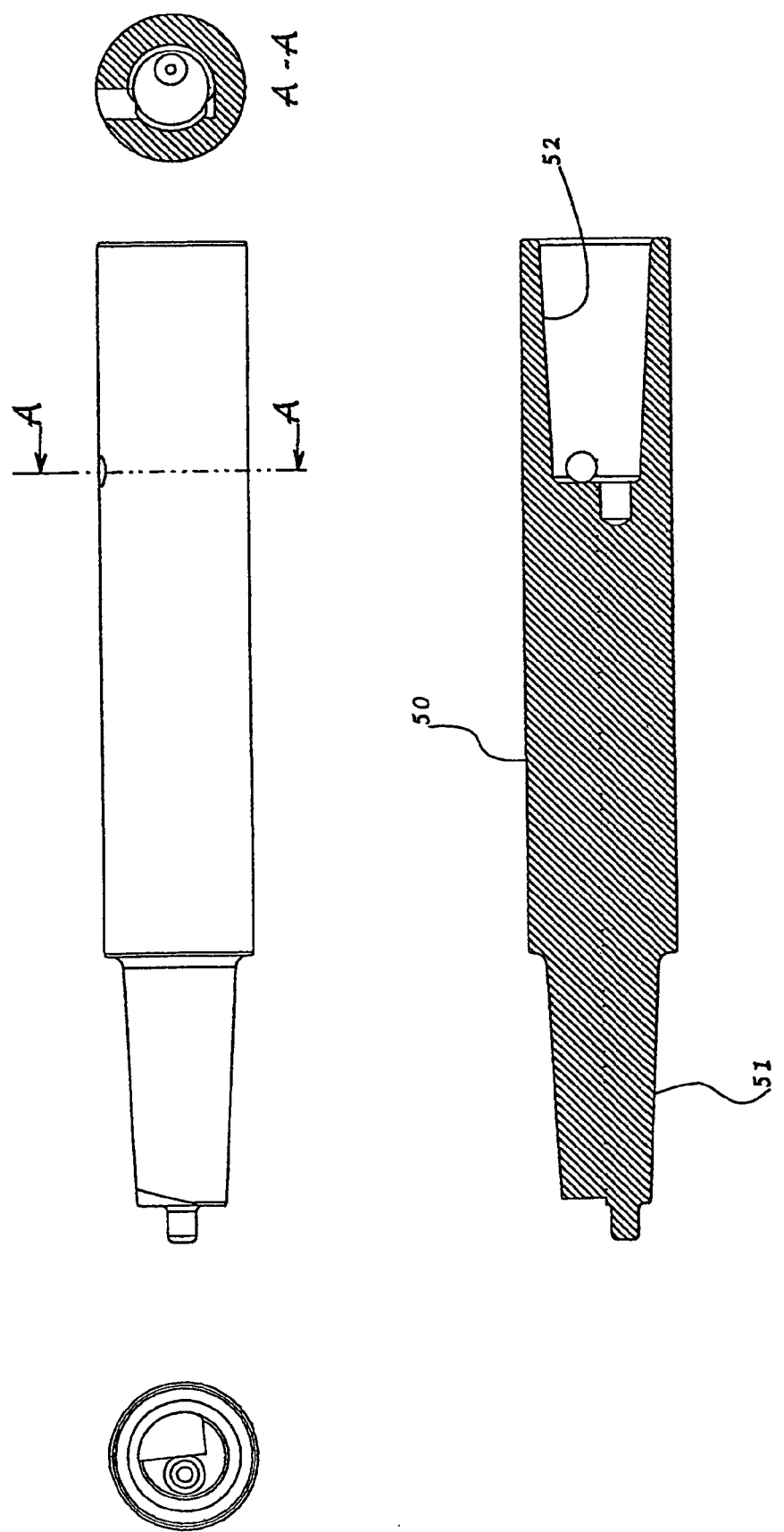

FIG. 7 shows a modular extension shaft which enables the total assemblies as shown in FIGS. 1 and 2 to be extended. Modular extension shaft 50 has male and female tapers at opposite ends which correspond respectively with taper 7 of the modular shaft and taper 42 of the modular stem. Of course, modular extension shaft 50 may be used in conjunction with a standard shaft or alone to connect the trochanter component 1 or condular member 21 with the stems 8.

Although not shown in detail, the prosthesis shown in FIGS. 1 and 2 can be combined by omitting the shafts 8 and collars 10 to form a complete femoral replacement prosthesis. Also, analogously formed components could be employed to replace another long bone such as the humerus.

As described above, the components of the prosthesis can be readily dismantled by using a disassembly tool inserted in the transverse walls in the components at each tapered join either after a trial assembly or in a revision operation.

The material preferably used is a titanium alloy throughout except for the femoral heads where cobalt chromium or ceramic heads are preferably used.

The invention claimed is:

1. A prosthesis for partial replacement of a long bone in humans and animals, said prosthesis comprising:
   an end component having an internal inwardly tapered recess having an open end;
   a shaft releasably coupled to said end component, said shaft having a first and second end and at least one notch, wherein said first end of said shaft is tapered and is dimensioned and configured for receipt within said internal inwardly tapered recess of said end component, and wherein said second end of said shaft has an internal inwardly tapered recess having an open end;
   a stem releasably coupled directly to said shaft, said stem having a longitudinal axis and a first and second end, wherein said first end is intended for engagement in a resected bone having a resected face, and said second end is tapered and is dimensioned and configured for receipt directly within said internal inwardly tapered recess of said second end of said shaft and wherein said tapered second end of said stem corresponds with said internal inwardly tapered recess of said shaft so that when said stem is coupled to said shaft, said tapered second end of said stem is received directly within said internal inwardly tapered recess of said second end of said shaft; and
   a collar releasably coupled to said shaft, said collar having first and second ends and an inwardly tapered recess, said recess of said collar having first and second open ends in said first and second ends of said collar respectively, the collar having at least one ear for cooperatively engaging said at least one notch on said shaft, when said collar is coupled to said shaft,
   wherein said second end of said shaft is outwardly tapered and is dimensioned for receipt within said recess of said collar via said first open end of said collar, and wherein an axial length of said shaft is dimensioned such that the second end of said collar abuts the resected face of the bone when the prosthesis is implanted.

2. A prosthesis as claimed in claim 1, wherein the end face of said second end of the collar terminates inboard of the external dimension of said resected face of the bone.

3. A prosthesis as claimed in claim 1, wherein at least a portion of the collar has a surface treatment designed to encourage bone growth.

4. A prosthesis as claimed in claim 1, wherein at least a portion of the collar has an external taper towards said resected face of the bone.

5. A prosthesis as claimed in claim 3, wherein said portion of the collar is formed with an externally stippled surface or is coated with hydroxyapatite or other bone growth promoting material.

6. A prosthesis as claimed in claim 1, which is a proximal femoral replacement prosthesis, the prosthesis including a trochanter replacement component, assembled with a shaft or a stem.

7. A prosthesis as claimed in claim 6 in which the trochanter replacement component is shaped to correspond approximately with an anatomical trochanter and includes a femoral neck for receiving a femoral ball and a generally flat face opposite the femoral neck for connection to residual bone or soft tissue.

8. A prosthesis as claimed in claim 7 in which said generally flat face carries stipples for engagement with residual bone.

9. A method of installing a prosthesis for partial replacement of a long bone in humans and animals, comprising the steps of:

i) providing a prosthesis having, an end component having an inwardly tapered recess having an open end;

a shaft releasably coupled to said end component, said shaft having a first and second end and at least one notch, wherein said first end of said shaft is outwardly tapered and is dimensioned and configured for receipt within said recess of said end component, and wherein said second end of said shaft has an inwardly tapered recess having an open end;

a stem releasably coupled directly to said shaft, said stem having a longitudinal axis and a first and second end, wherein said first end is intended for engagement in a resected bone having a resected face, and said second end is outwardly tapered and is dimensioned and configured for receipt directly within said recess of said second end of said shaft; and a collar releasably coupled to said shaft, said collar having first and second ends and an inwardly tapered recess, said recess of said collar having first and second open ends in said first and second ends of said collar respectively, the collar having at least one ear for cooperatively engaging said at least one notch on said shaft, when said collar is coupled to said shaft, wherein said second end of said shaft is outwardly tapered and is dimensioned for receipt within said recess of said collar via said first open end of said collar, and wherein an axial length of said shaft is dimensioned such that the second end of said collar abuts the resected face of the bone when the prosthesis is implanted, and ii) implanting said stem in a resected bone and assembling said stem, shaft, end component and collar such that said second end of said collar abuts the resected face of the bone when the prosthesis is implanted.

* * * * *

UNITED STATES PATENT AND TRADEMARK OFFICE
CERTIFICATE OF CORRECTION

PATENT NO. : 7,662,189 B2 Page 1 of 1
APPLICATION NO. : 11/433953
DATED : February 16, 2010
INVENTOR(S) : Jay Meswania It is certified that error appears in the above-identified patent and that said Letters Patent is hereby corrected as shown below:

Title Page, below Item (63) Related U.S. Application Data, insert:

-- (30)  Foreign Application Priority Data

December 15, 2000 (GB)          0030643.1 --

Signed and Sealed this

Twenty-fourth Day of August, 2010

David J. Kappos
*Director of the United States Patent and Trademark Office*